(12) United States Patent
Weber

(10) Patent No.: US 6,328,868 B1
(45) Date of Patent: Dec. 11, 2001

(54) METHOD FOR CARRIER-FREE DEFLECTION ELECTROPHORESIS

(76) Inventor: Gerhard Weber, Klausnerring 17, D-85551 Kirchheim (DE)

( * ) Notice: Subject to any disclaimer, the term of this patent is extended or adjusted under 35 U.S.C. 154(b) by 0 days.

(21) Appl. No.: 09/380,621

(22) PCT Filed: Mar. 20, 1998

(86) PCT No.: PCT/EP98/01648

§ 371 Date: Sep. 17, 1999

§ 102(e) Date: Sep. 17, 1999

(87) PCT Pub. No.: WO98/43077

PCT Pub. Date: Oct. 1, 1998

(30) Foreign Application Priority Data

Mar. 21, 1997 (DE) .............................................. 197 11 898

(51) Int. Cl.[7] .................................................. G01N 27/26
(52) U.S. Cl. ......................................................... 204/450
(58) Field of Search .................................... 204/450, 554, 204/600, 660; 210/748

(56) References Cited

U.S. PATENT DOCUMENTS 3,847,773   11/1974   Snyder ................................. 204/550

FOREIGN PATENT DOCUMENTS 41 39 472   3/1993   (DE) .

Primary Examiner—Jill Warden
Assistant Examiner—Alex Noguerola
(74) Attorney, Agent, or Firm—Nixon Peabody LLP; David S. Safran

(57) ABSTRACT

The invention relates to a method for carrier-free deflection electrophoresis, in which a separating agent used as carrier and a sample to be examined flow through a separating chamber (1) from an admission end to an outlet end, and the sample is physically separated into fractions, which are to be collected, by an electrode-generated electric field. The method is characterized in that the entry of the sample into a separating chamber between the electrodes occurs in the absence of voltage in the electrodes; in that voltage is applied to the electrodes after the sample has entered the separation area; and in that the electrophoretic separation is conducted only as long as the whole sample is essentially located in the separating area between the electrodes.

8 Claims, 5 Drawing Sheets

(State of the Art)

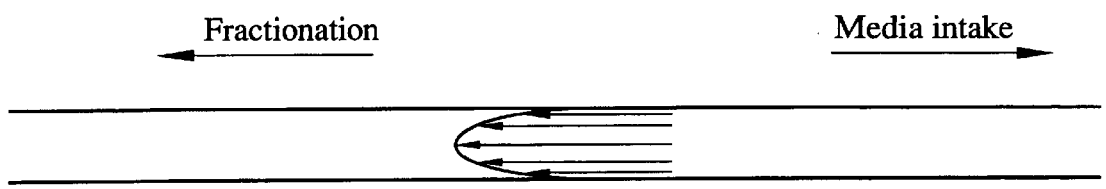
FIG.2.1
FIG.2.2

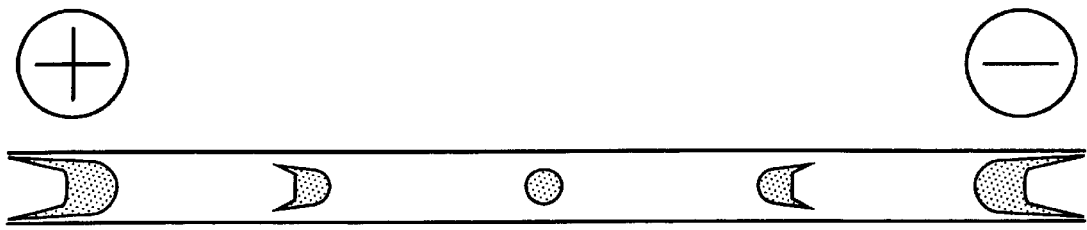
*FIG.3.1*
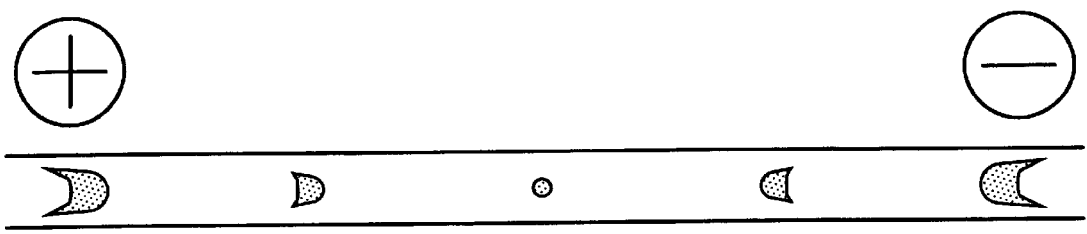
*FIG.3.2*
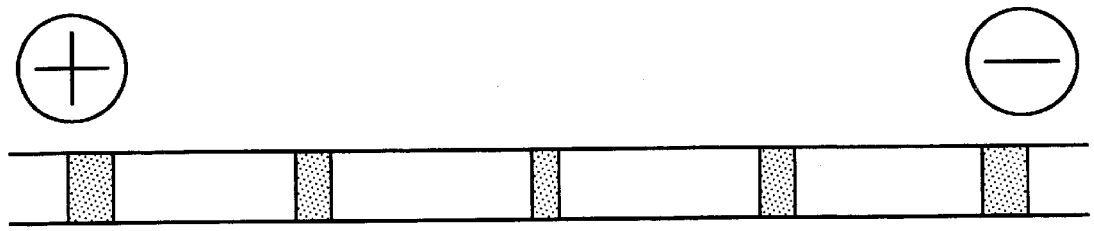
*FIG.3.3*

*FIG.4.1* *FIG.4.2* *FIG.4.3*
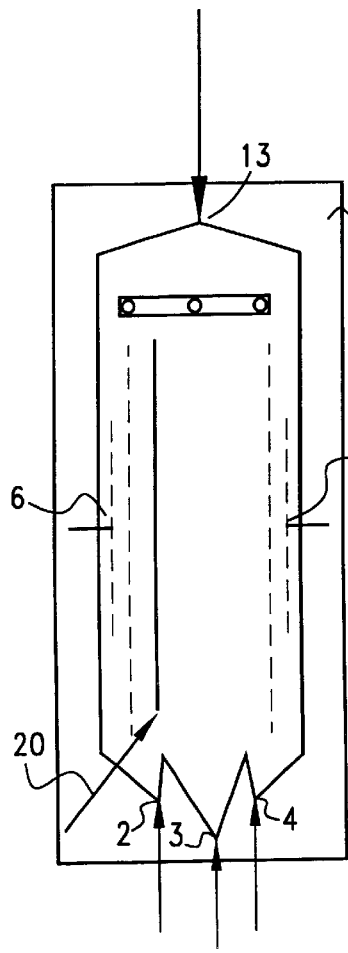 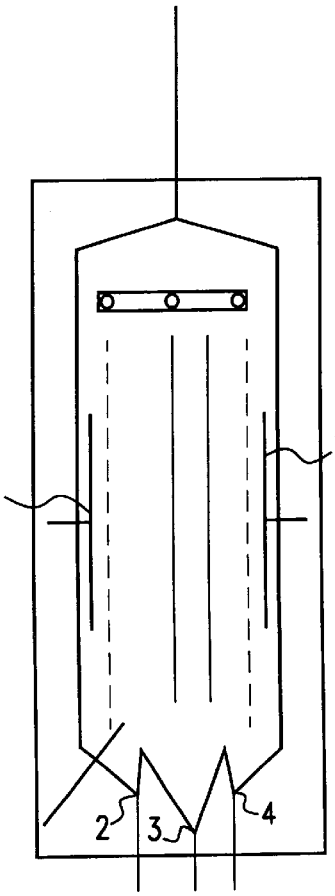 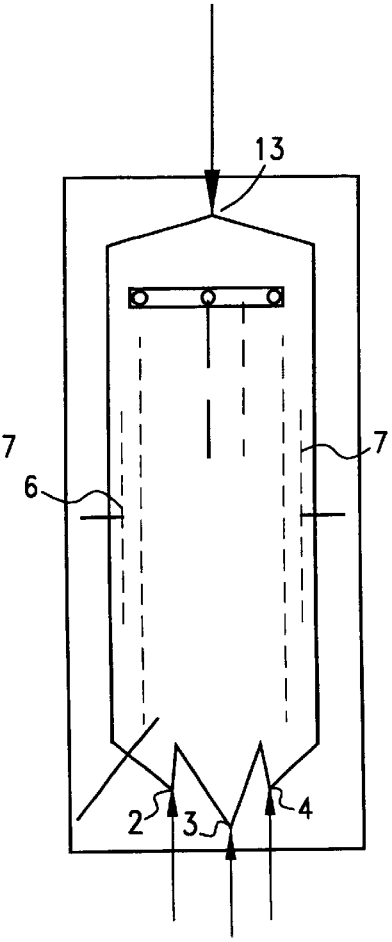

METHOD FOR CARRIER-FREE DEFLECTION ELECTROPHORESIS

BACKGROUND OF THE INVENTION

1. Field of the Invention

The invention relates to carrier-free deflection electrophoresis.

2. Description of the Related Art

Carrier-free deflection electrophoresis has previously been used exclusively in continuous processes. This process in fact yields outstanding results in a continuous operation if the negative influence of the laminar flow profile on the bandwidth of the substances to be separated can be minimized or not even come into play. This applies in particular to the process of continuous isoelectric focusing.

In all electromigration processes of deflection electrophoresis, the widening of the band caused by the laminar flow profile of the separating medium (media) triggers a serious deterioration in separation capacity.

The basics of carrier-free deflection electrophoresis in continuous processes were already described in the literature over 30 years ago, including in the 1968 yearbook of the Max-Planck company on pp. 117–137. This process is also described under the term FFE (free flow electrophoresis) or CFE (continuous flow electrophoresis). (K. Hannig: Carrier-free continuous electrophoresis and its application. Anal. Chem. 181, 233 (1961); M. C. Roman and P. R. Brown: Anal. Chem. Free Flow Electrophoresis. 66(N2), 86–94, (1994); R. Braun, H. Wagner and G. Weber: Preparative Free Flow Electrophoresis—a powerful procedure for separating natural substances, GIT Fachzeitschrift für das Laboratorium 39 (1995), 317–322).

FFE separation procedures are used to separate ions of any molecular weight up to bioparticles. It is here irrelevant whether the sample to be separated is charged itself, or whether the charge came about via the addition or sorption of ions.

SUMMARY OF THE INVENTION

This process is used for both preparative and analytical separations.

The applicant has improved essential aspects of the method for continuous deflection electrophoresis (German Patent DE 41 39 472 C1).

The order of magnitude of these improvements varied for the different FFE separation techniques:

In all FFE separation techniques, a distinct improvement in long-term stability was achieved for the separation.

The separation capacity was improved by a factor of 10–50 for continuous isoelectric focusing, while only an improvement by a factor of 2–4 was reached in the electromigration process, and this improvement was exclusively reached via the novel "dead volume-free" fractionation using the counterflow as described in the patent. The negative influence of the laminar flow profile on the separation capacity of the electromigration processes was not influenced by the aforementioned improvements.

A method for continuous deflection electrophoresis will be described below based on the "typical" electromigration process, the zone electrophoresis.

FIG. 1 presents a schematic view of a separation chamber 1. Located at the lower end of separation chamber 1 are at least three inlet holes 2, 3, 4, which are connected with the conveyance channels of a multi-channel pump 5 by means of three lines. The separation medium is introduced into the separating space via central inlet hole 3, while the stabilization media are introduced via the two outside inlets 2, 4.

These media flow through the separating space under laminar flow conditions. Situated parallel to the side edges of the separation chamber are electrodes 6, 7, which are rinsed in circulation by an additional pump with a high flow rate. Membranes 8, 9, which conduct electrical current, separate the electrode spaces from the separating space, and prevent any exchange of media via the hydrodynamic flow.

If a sample mixture is now introduced into the flowing separation medium using an independent metering pump 10 at the optimal metering rate, this sample is transported with the separation medium as a fine jet.

If a high voltage is applied to the electrodes, all charged constituents in the media and sample are deflected out of the original direction, with this deflection increasing as do the number of charges possessed by these ionic constituents.

Constituents of varying charge hence migrate along separate paths (see FIG. 1) through the separating space, and reach a row of hose openings 11 arranged transverse to the direction of flow at different locations, after which they are routed to separate collecting basins 12 with the media. This series of hose openings with the smallest possible distance between the openings is referred to as a fractionating device, and the number of these hoses arranged in parallel ranges between 30 and a maximum of 180.

An additional medium (counterflow medium) flows from the top end of the separation chamber in an opposite direction via an inlet 13 to the separation media, and also exits the separating space via the hose openings of the fractionating device.

A device conceived in accordance with the above description yields separations that exhibit an outstanding long-term stability for the separation profiles in all separation techniques of continuous deflection electrophoresis, but the quality of separation (resolution) can be compared with the level attained in the analogous analytical separation technique only in the case of continuous isoelectric focusing.

By contrast, in all continuous electromigration processes, the separation capacity is modest in comparison with the analogous analytical separation techniques.

Numerous publications describe the physical or electrochemical effects that contribute to the so-called band widening of the analytes during separation in continuous deflection electrophoresis (J. A. Giannovario, R. Griffin, E. L. Gray: A mathematical model of free-flow electrophoresis. Journal of Chromatography, 153, 329–352 (1978); F. G. Boese: Contribution to a mathematical theory of free flow electrophoresis, J. Chromat. 483, 145–170 (1988); K. Hannig and H. G. Heidrich: Free-Flow Electrophoresis, 1990 by GIT Verlag Darmstadt ISBN 3-921956-88-9).

The most important of these effects are:

widening due to the laminar flow profile, widening due to thermal convection, widening due to electrical osmosis, widening due to electrokinetic effects.

The negative influence of all electrokinetic effects described thus far can be minimized or eliminated by using separation media with suitable ionic constituents with sufficiently high ionic strength, and at the same time not excessively increasing the concentration of the sample.

There are numerous ways to minimize the negative influence of electrical osmosis, e.g., through the selection of a suitable wall material (plastics instead of glass or quartz), or most preferably by adding surface-active chemicals to the separation media that preclude electrical osmosis. This method is referred to as "dynamic coating" in the literature.

The negative influence of thermal convection can be reduced very easily by arranging the separation chamber horizontally instead of vertically.

The negative influence of the laminar flow profile does not exist for continuous isoelectric focussing as long as a sufficiently long separation time is selected that also enables the focussing of the analytes, which are transported at the highest linear velocity in the center of the separation chamber gap.

By contrast, the negative influence is very significant in the case of the electromigration processes. Analytes that migrate near or in the boundary surface to the walls of the separation chamber pass through the separation chamber in a considerably longer time than analytes at the center of the separation chamber gap (see FIGS. 2.1 and 2.2), and are hence deflected to a clearly greater extent. This effect results in a band widening detectable as a tailing in the direction of electromigration. FIG. 3.1 depicts this effect of band widening for 2 low-molecular analytes with opposite charges, while FIG. 3.2 illustrates the same for high-molecular particles.

Given a continuously executed electromigration process under the boundary conditions of carrier-free electrophoresis, then, the negative influence of the laminar flow profile cannot be averted for low-molecular analytes. The absolute value of band widening increases as does the migration distance of the analytes. Reducing the diffusion by using separation media with increased viscosity also does not help, since this makes the laminar flow profile even more unfavorable (FIG. 2.2).

In the case of separation of bioparticles, a quantitatively reduced sample feeding to the center of the separation chamber gap can result in an improved resolution, since the particles cannot get into the area of the separation chamber walls during a retention time of <10 minutes due to the extremely low diffusion (see also FIG. 3.2). The influence of laminar flow profile can only be minimized in this way by distinctly reducing the sample throughput (by a factor of 0.3–0.05).

The object of the invention is to specify a method for carrier-free deflection electrophoresis, which eliminates the influence of a laminar flow profile.

The object is achieved according to the invention by means of a method with the features set forth in claim 1. Advantageous embodiments of the invention are the subject-matter of the dependent claims.

The process according to the invention involves interval operation, wherein the sample is introduced in the separation space with the electrical field deactivated, after which electrophoretic separation is performed at most for as long as all parts of the sample still remain in the electrical field. This process overcomes the disadvantage to the continuous process in which a laminar flow profile with lower flow rates in the area of the separation chamber walls leads to varying retention times of different parts of the sample in the electrical field, and hence to a diminished resolution.

To ensure sufficiently high sample quantities while simultaneously limiting the length of the electrodes in the direction of flow, it is preferred to perform electrophoretic separation with the sample and carrier medium at rest, or at least at a greatly diminished flow rate as compared to that while introducing the sample, equivalent to a slow drifting of the sample in the separating space toward the outlet.

In the known method, the sample is continuously added together with the separation or carrier medium, and electrophoretic separation is performed continuously with the electrical field continuously activated. In the invention, at least the sample is instead introduced discontinuously with the electrical field deactivated, and electrophoretic separation is preferably performed with the sample at rest together with the separation medium or with the sample drifting slowly together with the separation medium, and only for as long as all parts of the sample still remain in the separating space. In this way, the various flow rates of different parts of the sample are prevented from influencing the electrophoresis result, and the resolution is improved accordingly.

An embodiment of the invention is described below based on the attached drawings.

BRIEF DESCRIPTION OF THE DRAWINGS

FIG. 2.1 is a laminar flow profile for media with a relatively low viscosity, wherein a separation chamber gap is shown in a section encompassing the flow direction;

FIG. 2.2 is a laminar flow profile for media with elevated viscosity, wherein a separation chamber gap is shown in a section encompassing the flow direction;

FIG. 3.1 is band widening based on the separation of an anionic and cationic analyte with a high diffusion rate, wherein the separation chamber gap is shown in a section perpendicular to the flow direction;

FIG. 3.2 is band widening based on the separation of an anionic and cationic analyte with low diffusion rate, wherein the separation chamber gap is shown in a section perpendicular to the flow direction;

FIG. 3.3 is band widening based on the separation of an anionic and cationic analyte with a high diffusion rate during the FFE separation process executed in accordance with the invention, wherein the separation chamber gap is shown in a section perpendicular to the flow direction;

FIGS. 4.1, 4.2 and 4.3 show the time progression for an embodiment of the method according to the invention in the device shown on FIG. 1, wherein FIG. 4.1 depicts the initial stage with medium and sample introduction with the electrical field set to zero, FIG. 4.2 depicts the subsequent stage with activated electrical field, without medium and sample transport, and FIG. 4.3 depicts the subsequent stage of medium introduction and sample removal with the electrical field deactivated.

DETAILED DESCRIPTION OF THE INVENTION

Figure 1:
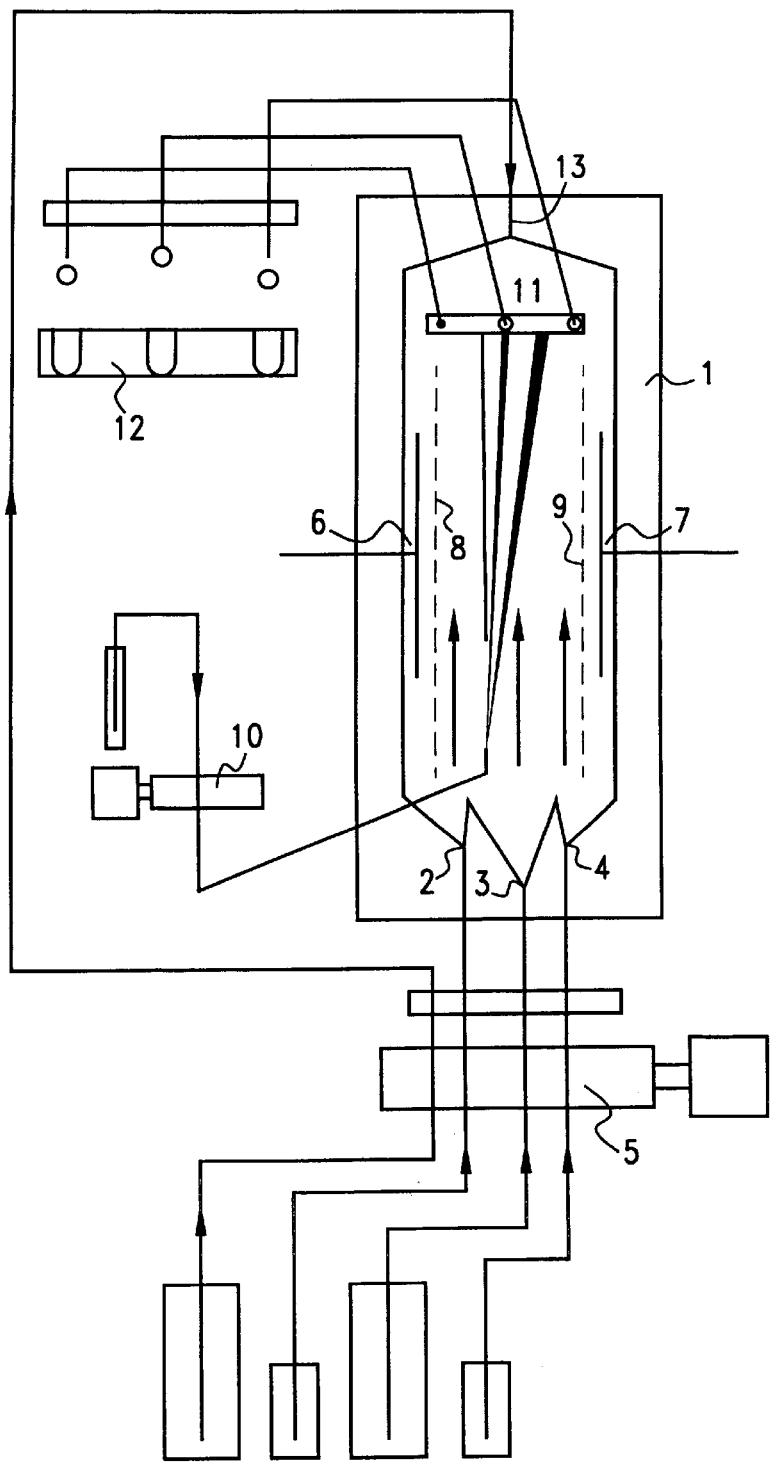
FIG. 1 is a known apparatus for performing deflection electrophoresis.

FIGS. 4.1 to 4.3 show the same separation chamber 1 depicted in FIG. 1, also in schematic form. The same parts shown in FIG. 1 are marked with the identical reference signs as there.

In the initial phase shown on FIG. 4.1, the separation medium is introduced into the separating space via central inlet hole 3, while the stabilization media are introduced into the separating space via two outside inlets 2 and 4. At the same time, the counterflow medium flows in via inlet 13. The sample is introduced via an inlet 20. No voltage is applied between electrodes 6 and 7 (denoted by the electrodes represented by dashed lines).

The sample then expands essentially parallel to the electrodes (denoted by the vertical line proceeding from the tip of the arrow running through inlet 20).

In the next phase shown on FIG. 4.2, a voltage is applied to electrodes 6 and 7, so that an electrical field (with a horizontal field direction in the drawing) is formed in the separation chamber. Media and sample transport is interrupted, and the sample constituents are spatially separated in the horizontal direction in the drawing (denoted by the two vertical parallel continuous lines on FIG. 4.2).

In the final phase shown on FIG. 4.3, the electrical field is again deactivated, and the media are again introduced via the inlets 2, 3 and 4 and 13, but not the sample. In this way, the electrphoretically spatially separated sample constituents are carried away via hose openings 11.

As long as it is ensured that the sample introduced between electrodes 6 and 7 in the first phase remains in the electrical field with all its parts during the ensuing phase of electrophoretic separation, the sample can be allowed to drift slowly, and even to flow at the same rate as when introduced given suitably dimensioned electrodes, instead of remaining at rest during the electrophoretic separation.

Executing the procedure in the interval mode in accordance with the invention results in a clear improvement in resolution in comparison to the known continuous process.

This can be illustrated by separating a mixture of electrically charged dyes, once via continuous free flow electrophoresis, and then with discontinuous free flow zone electrophoresis according to the invention.

Figure 5:
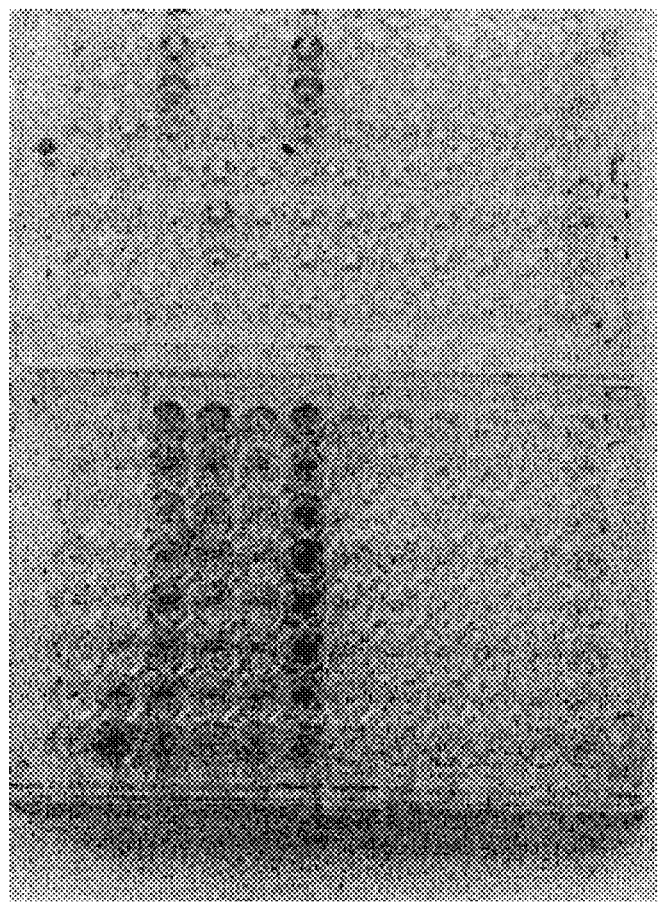
FIG. 5 shows a comparison of distribution patterns for the separated analytes in the method according to the invention (top) and in the continuous process (bottom).

FIG. 5 shows a comparison of distribution patterns of the separated analytes in the respective collecting basins (microtiter plate cavities) during the procedure according to the invention, and for the known continuous process. In the case of interval operation according to the invention (result at top of figure), the separation quality is equally good for all analytes, and far better than in the comparison test of the continuous process (result at bottom of figure).

The comparison was performed using the same apparatus and under comparable electrophoretic conditions (identical separation medium, similar electrophoretic migration path, similar electrophoretic capacity).

Since a significantly shorter separation time is sufficient in the interval mode to achieve a separation quality of the level possible during the continuous process, a higher throughput can be achieved during interval operation as well.

The reason for the improved resolution during interval operation as opposed to continuous operation is evident from FIGS. 3.1 to 3.3, which show sections through the separation chamber perpendicular to the flow direction and parallel to the direction of the electrical field.

FIGS. 3.1 and 3.2 show band widening in continuous operation for an anionic and cationic analyte with high diffusion rate, or for an anionic and cationic analyte with low diffusion rate. FIG. 3.3 shows band widening for the anionic and cationic analyte with high diffusion rate in the case of standing media.

During continuous operation, band widening comes about due to the laminar flow cross section (compare FIG. 2.1), which results in higher retention times for the analyte in the electrical field, and hence a stronger lateral migration in the area of the separation chamber walls. This triggers an additional sickle-shaped band widening that is superposed over band widening via diffusion.

During interval operation, where the electrical field acts on a standing analyte, band widening is caused solely through diffusion, and hence is lower than in cases of continuous operation. Lower band widening leads to a higher resolution. Therefore, resolution is better in interval operation than in continuous operation.

What is claimed is:

1. A method for carrier-free deflection electrophoresis comprising the steps of:

causing a separation medium carrying a sample to be analyzed to flow through a separation chamber from an inlet end thereof to an outlet end thereof, and spatially separating the sample into fractions to be collected using an electrical field generated by electrodes; wherein the sample is introduced into a separating space lying between the electrodes when no voltage is applied to the electrodes; wherein voltage is applied to the electrodes after the sample has been introduced into the separating space; wherein the separation medium and the sample travel at a flow rate that is reduced between the electrodes from an initial flow rate at the inlet end to a slow drifting in a direction toward the outlet end; and wherein electrophoretic separation is performed only when the entire sample is located in the separating space between the electrodes.

2. The method according to claim 1 comprising the further steps of using an external detector to determine that a sample constituent or marker substance has reached a predetermined position in the separation chamber, and concluding the electrophoretic separation as soon as the external detector has determined that the sample constituent or marker substance has reached said predetermined position in the separation chamber.

3. The method according to claim 2, comprising the further step of transporting the separated sample fractions into separate sample containers via a fractionating device at a high flow rate with the electrical field deactivated.

4. The method according to claim 1 comprising the further step of transporting the separated sample fractions into separate sample containers via a fractionating device at a high flow rate with the electrical field deactivated.

5. A method for carrier-free deflection electrophoresis comprising the steps of:

causing a separation medium carrying a sample to be analyzed to flow through a separation chamber from an inlet end thereof to an outlet end thereof, and spatially separating the sample into fractions to be collected using a field generated by electrodes; wherein the sample is introduced into a separating space lying between the electrodes when no voltage is applied to the electrodes; wherein voltage is applied to the electrodes after the sample has been introduced into the separating space; and wherein electrophoretic separation is performed with the sample being at rest with the separation medium in the separating space between the electrodes.

6. The method according to claim 5, comprising the further steps of using an external detector to determine that a sample constituent or marker substance has reached a predetermined position in the separation chamber, and concluding the electrophoretic separation as soon as the external detector has determined that the sample constituent or marker substance has reached said predetermined position in the separation chamber.

7. The method according to claim 6, comprising the further step of transporting the separated sample fractions into separate sample containers via a fractionating device at a high flow rate with the electrical field deactivated.

8. The method according to claim 5, comprising the further step of transporting the separated sample fractions into separate sample containers via a fractionating device at a high flow rate with the electrical field deactivated.

* * * * *